(12) United States Patent
Berker et al.

(10) Patent No.: US 10,542,956 B2
(45) Date of Patent: Jan. 28, 2020

(54) ESTIMATION OF AN ATTENUATION MAP BASED ON SCATTERED COINCIDENCES IN A PET SYSTEM

(71) Applicant: KONINKLIJKE PHILIPS N.V., Eindhoven (NL)

(72) Inventors: Yannick Berker, Witten (DE); Volkmar Schulz, Wuerselen (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 247 days.

(21) Appl. No.: 15/570,758

(22) PCT Filed: May 10, 2016

(86) PCT No.: PCT/EP2016/060363
§ 371 (c)(1),
(2) Date: Oct. 31, 2017

(87) PCT Pub. No.: WO2016/184712
PCT Pub. Date: Nov. 24, 2016

(65) Prior Publication Data
US 2018/0116621 A1 May 3, 2018

(30) Foreign Application Priority Data
May 19, 2015 (EP) .................................... 15168181

(51) Int. Cl.
*A61B 6/00* (2006.01)
*A61B 6/03* (2006.01)
(Continued)

(52) U.S. Cl.
CPC ............ *A61B 6/5282* (2013.01); *A61B 6/037* (2013.01); *A61B 6/4417* (2013.01);
(Continued)

(58) Field of Classification Search
CPC .............................. A61B 6/5282; A61B 6/032
See application file for complete search history.

(56) References Cited

U.S. PATENT DOCUMENTS 9,734,600 B2 8/2017 Berker
2015/0098640 A1 4/2015 Berker
2015/0119694 A1 4/2015 Mihlin

OTHER PUBLICATIONS

Berker, et al., "Scattered PET data for attenuation-map reconstruction in PET/MRI", Medical Physics, vol. 41, No. 10, Oct. 1, 2014.
(Continued)

*Primary Examiner* — Joseph M Santos Rodriguez

(57) ABSTRACT

The invention relates to a system for generating an estimate of a photon attenuation map for an object on the basis of single-scattered coincidences measured in a PET scanner. The system comprises a simulation module configured to calculate single-scattered coincidences by a numerical model calculation based on a preliminary attenuation map, where the estimate of the photon attenuation map is generated by adapting at least some attenuation values. The model calculation is made on the basis of a grid covering the object, the grid comprising grid elements (61) to which attenuation values are assigned, and the simulation module is further configured to determine at least one set of adjacent grid elements (61) in order to form a merged image element (63) including the set of adjacent grid elements (61) and to assign a single attenuation value to the merged image element in the model calculation.

15 Claims, 4 Drawing Sheets

(51) Int. Cl.
    *G01R 33/48* (2006.01)
    *G06T 7/00* (2017.01)
    *G06T 11/00* (2006.01)
(52) U.S. Cl.
    CPC .......... *A61B 6/5205* (2013.01); *A61B 6/5247* (2013.01); *G01R 33/481* (2013.01); *G06T 7/0012* (2013.01); *G06T 11/006* (2013.01); *G06T 2207/10088* (2013.01); *G06T 2207/10104* (2013.01)

(56) References Cited

OTHER PUBLICATIONS

Salomon, et al., "Simultaneous Reconstructions of Activity and Attenuation for PET/MR", IEEE Transactions on Medical Imaging, vol. 30, No. 3, Mar. 1, 2011.
Nuyts et al., "Simultaneous maximum a posteriori reconstruction and activity distribution from emission sinograms", IEEE Trans. Med. Imaging 18 (1999), 393-403.
Defrise, et al., "Time-of-flight PET data determine the attenuation sinogram up to a constant", Phys. Med. Biol. 57 (2012) 885-899.
Conti, et al., "Reconstruction of scattered and unscattered PET coincidences using TOF and energy information", Phys. Med. Biol. 57 (2012) N307-N317.

ESTIMATION OF AN ATTENUATION MAP BASED ON SCATTERED COINCIDENCES IN A PET SYSTEM

CROSS REFERENCE TO RELATED APPLICATIONS

This application is the U.S. National Phase application under 35 U.S.C. § 371 of International Application No. PCT/EP2016/060363, filed May 10, 2016, published as WO 2016/184712 on Nov. 24, 2016, which claims the benefit of European Patent Application Number 15168181.4 filed May 19, 2015. These applications are hereby incorporated by reference herein.

FIELD OF THE INVENTION

The invention relates to a method and a system for generating an estimate of a photon attenuation map on the basis of measurements of single-scattered coincidences in a Positron Emission Tomography (PET) system. Moreover, the invention is related to a computer program causing a processor to carry out the method.

BACKGROUND OF THE INVENTION

In PET, a positron-emitting substance is injected into a human or animal body or into another object to be monitored. The substance, which is usually also referred to as radio pharmaceutical or radiotracer, is selected such that it is adsorbed in certain regions of the object, e.g. in regions which are of interest for the diagnosis of certain diseases. For instance, the substance may be adsorbed by tumor cells so that such cells can be detected in PET images of a human or animal body.

When a positron is emitted by the radiotracer, an encounter with a nearby electron annihilates the electron positron pair and produces a pair of annihilation photons. Each of these annihilation photons has an energy of 511 keV and both photons travel in substantially opposite directions. These photons are recorded by the PET detector substantially at the same time as a so-called coincidence. From such coincidences, PET systems reconstruct a so-called activity distribution or activity map, which shows the spatial distribution of the electron positron annihilation rate within the object. The activity distribution substantially corresponds to the spatial distribution of the radiotracer within the object, which can thus be evaluated for diagnostic or other purposes.

Usually, the activity distribution is determined on the basis of true coincidences, i.e. coincidences comprising two annihilation photons that travel unimpeded to the PET detector and hit the detector at opposing locations with their original energy of 511 keV. However, it is not possible to reconstruct the activity map based on the true coincidences alone, because not all annihilation photons reach the detector unimpeded due to photon attenuation. Attenuation particularly occurs when a photon is absorbed before it reaches the detector or when it undergoes inelastic Compton scattering one or more times (where a scattered photon may reach the detector but has a lower energy). In order to take account of these effects, attenuation correction has to be performed when determining the activity map. Without such attenuation correction, regions having a high activity and a high attenuation probability for photons originating from this region would appear as regions with a smaller activity.

Attenuation correction requires the knowledge of a so-called attenuation map or attenuation distribution, which provides the spatial distribution of the photon attenuation rate. In combined PET and Computed Tomography (CT) imaging system, such an attenuation map is readily available. So, the CT images correspond to attenuation maps for X-ray photons and can be up-scaled to the energy of the annihilation photons. Also for standalone PET systems and systems combining PET with a different imaging modality than CT, such as for example Magnetic Resonance Imaging (MRI), techniques for determining the attenuation map have been developed. One approach, which is also referred to as Maximum-Likelihood Reconstruction of Attenuation and Activity (MLAA) is particularly described in the publication J. Nuyts et al., "Simultaneous maximum a posteriori reconstruction and activity distribution from emission sinograms", IEEE Trans. Med. Imaging 18 (1999), 393-403. In this approach, both the activity distribution and the attenuation map are reconstructed from PET measurement data. However, this approach does usually only allow to determine relatively rough estimates of the attenuation map.

A further technique for determining the attenuation map is described in the publication Y. Berker, F. Kiessling and V. Schulz, "Scattered PET data for attenuation-map reconstruction in PET/MRI", Med. Phys. 41 (10), October 2014, 102502. In accordance with this technique, an estimate of the attenuation map is reconstructed on the basis of single-scattered coincidences. These coincidences respectively include one annihilation photon reaching the PET detector unimpeded and one annihilation photon that is scattered a single time. In order to determine the attenuation map, the single-scattered coincidences are calculated by means of a model calculation on the basis of an estimate of the attenuation map, and the calculated single-scattered coincidences are compared with the measured single-scattered coincidences. On the basis of this comparison an attenuation map minimizing the difference between the calculated and measured single scattered coincidences is determined. For this purpose an iterative procedure is applied.

This technique allows for a relatively precise estimate of the attenuation map. However, the technique involves a high computational complexity. So, the calculation of single-scattered coincidences is a numerical calculation performed on the basis of a grid that divides the detector volume into grid elements, which are usually also referred to as voxels. For the calculation of the single-scattered coincidences, one attenuation value from the estimate of the attenuation map is assigned to each voxel. This leads to a large number of required calculation steps, which makes the technique relatively slow and impedes its use in practical applications.

SUMMARY OF THE INVENTION

Therefore, it is an object of the present invention to allow for determining estimates of the attenuation map on the basis of single-scattered coincidences with a reduced computational complexity.

In a first aspect of the invention, a system for generating an estimate of a photon attenuation map for an object is suggested. The system comprises a PET scanner configured to measure single-scattered coincidences originating from the object, the single-scattered coincidences comprising one unscattered photon and one photon scattered one time. Further, the system comprises a simulation module configured to calculate single-scattered coincidences by a numerical model calculation based on a preliminary attenuation map and an estimate of an activity map, the model calculation being made on the basis of a regular grid covering the object, the grid comprising a plurality of grid elements to which attenuation values are assigned in accordance with the preliminary attenuation map, and the system comprises an evaluation unit configured to generate the estimate of the photon attenuation map by adapting at least some attenuation values on the basis of a comparison between the calculated single-scattered coincidences and the measured single-scattered coincidences. The simulation module is further configured to determine at least one set of adjacent grid elements on the basis of information obtained independent of the single-scattered coincidences in order to form a merged image element including the set of adjacent grid elements and to assign a single attenuation value to the merged image element in the model calculation.

By merging adjacent grid elements to form a merged image element to which a single attenuation value is assigned, the number of individual attenuation values to be considered in the model calculation is reduced. Hereby, also the number of calculation steps and, thus, the computational complexity is reduced.

Thus, compared with the conventional system, the model calculation is not exclusively made on the basis of the grid elements with respect to the attenuation value but on the basis of at least one merged image elements. Or, in other words, a discrete attenuation map on the basis of which the model calculation is carried out, does not exclusively include grid elements to which attenuation values are assigned but also at least one merged image element. Thus, the set of grid elements forming a merged image element is particularly considered as one single photon-attenuating element in the model calculation.

The determination of the at least one set of grid elements to which a single attenuation value is assigned is made on the basis of information that is obtained independent of the single-scattered coincidences. Such additional information may allow for forming merged image elements in accordance with predefined criteria. However, it may not be possible to allocate each grid element to one set of grid elements forming a merged image element. Therefore, one embodiment provides that the simulation module is further configured to assign an individual attenuation value to at least one grid element not included in the merged image element. Thus, the model calculation considers at least one photon-attenuating element, which consists of multiple grid elements, and photon-attenuating elements, which consist of single grid elements, in the aforementioned embodiment.

One possible criterion for merging adjacent grid elements to define the merged image element may be that the set of adjacent grid elements covers a region with substantially homogenous photon attenuation, i.e. a region including grid elements having approximately equal attenuation values. Hereby, it is ensured that a correct estimate of the photon attenuation map is determined on the basis of the merged image elements.

Such a region can particularly be determined on the basis of an evaluation of measured true coincidences. In particular, one embodiment comprises that the Positron Emission Tomography scanner is further configured to measure true coincidences, that the evaluation unit is configured to determine a further estimate of a photon attenuation map on the basis of the measurements of the true coincidences and that the simulation module is configured to determine the set of adjacent grid elements based on the further estimate of the photon attenuation map. In a related embodiment, the simulation module is configured to determine adjacent grid elements having approximately equal attenuation values in the further estimate of the photon attenuation map and to combine these grid elements to form the merged image element.

In a further embodiment, the system comprises a further scanner for imaging the object in accordance with a further modality different from PET, and the simulation module is configured to determine the set of adjacent grid elements based on an image of the object generated using the further scanner. The further scanner may particularly be a Magnetic Resonance Imaging scanner. In a related embodiment, the object is at least a part of a human or animal body and the simulation module is configured to identify within the object a region comprising tissue of the same tissue class in the image generated using the further scanner and to combine grid elements covering the identified region to form the merged image element.

These embodiments exploit the fact that MRI images usually allow for determining regions with homogenous photon attenuation within a human or animal body or another object. In case the object to be monitored is a human or animal body, these regions particularly correspond to regions including tissue of the same tissue class.

Moreover, one embodiment provides that the grid further covers a region outside the object, a portion of this region including the same material, and that the simulation module is configured to combine grid elements covering the portion of the region to form the merged image element. In this embodiment, it is also possible to merge grid elements located outside the object to form a merged image element. In particular, grid elements are merged which cover the same material and, thus, a region with homogenous photon attenuation. The material outside the object may particularly be included in appliances for supporting the object to be imaged or other appliances within the PET scanner. Moreover, the area of the PET scanner which is not occupied by the object or any appliance the same material, which is usually air.

In a related embodiment, a position of the portion of the region outside the object, which includes the same material, is preconfigured in the simulation unit and/or determined on the basis of the image, which is generated using the further scanner. With respect to this embodiment, the position may particularly be preconfigured in the simulation unit when material is included in appliances of the aforementioned type, which are located in the PET scanner at predetermined positions. On the basis of the image of the object generated using the further scanner, it is particularly possible to determine an outline of the object and thus determine an area between the object and the PET scanner which is usually filled with a single material, such as air, and to merge grid elements in this area to form a merged image element.

In accordance with a further possible criterion, adjacent grid elements which cover a region outside a certain region of interest are combined to a merged image element. Therefore, one embodiment provides that the simulation module is configured to identify grid elements corresponding to a predetermined region of interest within the object and to combine grid elements, which do not correspond to the predetermined region of interest, to form the merged image element. Hereby, the spatial resolution of the generated attenuation map is effectively reduced in the area comprising the merged grid elements, which is often acceptable outside the region of interest.

In a further embodiment, the evaluation unit is configured to determine the estimate of the photon attenuation map in a series of iteration steps, and in each iteration step the evaluation unit determines an updated attenuation map on the basis of a comparison between calculation single-scattered coincidences and the measured single scattered coincidences. In each iteration step, the calculation of the single-scattered coincidences is made on the basis of one estimate of the attenuation map, where in the first iteration step, the preliminary attenuation map is used as the estimate, and in subsequent iteration adapted attenuation maps are used as the estimate.

In a related embodiment, the evaluation unit is configured to determine in an iteration step a difference between the updated attenuation map and an attenuation map determined in a preceding iteration step, the difference being determined on the basis of a back-projection of a difference between the measured single-scattered coincidences and the calculated single-scattered coincidences.

Moreover, one embodiment provides that the system is configured to determine the estimate of the activity map on the basis of measured true coincidences.

Furthermore, one embodiment provides that the model calculation of the single-scattered coincidences is made in accordance with a relation $$S = \sum_{a,b} \lambda(a) M_{ab} \mu(b),$$

where S denotes a number of single-scattered coincidences measured at certain locations of a detector of the PET scanner with an energy of the scattered photon within a certain energy range, $\lambda(a)$ denotes an activity value assigned to a grid element a of the grid, $\mu(b)$ denotes an attenuation value assigned to a grid element b or merged image element b and $M_{ab}$ denotes a factor, wherein the sum is calculated on the basis of at least one merged image element b. The factor $M_{ab}$ does particularly weight the influence of an activity at the grid element a and a photon attenuation at the grid element or merged image element b on S.

When the model calculation is made on the basis of a relation of the aforementioned kind, the merging of grid elements to one or more merged image elements reduces the number of summands in the sum over b, thereby reducing the computational complexity of the numerical model calculation.

In a further aspect of the invention, a method for generating an estimate of a photon attenuation map for an object is proposed. The method comprises the steps of:
  operating a PET scanner to measure true coincidences and single-scattered coincidences originating from the object, the single-scattered coincidences comprising one unscattered photon and one photon scattered one time,
  calculating single-scattered coincidences by a numerical model calculation based on a preliminary attenuation map and an estimate of an activity map, the model calculation being made on the basis of a regular grid covering the object, the grid comprising a plurality of grid elements to which attenuation values are assigned in accordance with the preliminary attenuation map, and
  generating the estimate of the photon attenuation map by adapting at least some attenuation values on the basis of a comparison between the calculated single-scattered coincidences and the measured single-scattered coincidences,
wherein at least one set of adjacent grid elements is determined on the basis of information obtained independent of the single-scattered coincidences to form a merged image element including the set of adjacent grid elements and a single attenuation value is assigned to the merged image element in the model calculation.

In a still further aspect, a computer program is suggested. The computer program is executable in a processing unit of a system as defined in claim 1, and the computer program comprises program code means for causing the processing unit to carry out a method as defined in claim 14.

It shall be understood that the device of claim 1, the method of claim 14 and the computer program of claim 15 have similar and/or identical preferred embodiments, in particular, as defined in the dependent claims.

It shall be understood that a preferred embodiment of the present invention can also be any combination of the dependent claims or above embodiments with the respective independent claim.

These and other aspects of the invention will be apparent from and elucidated with reference to the embodiments described hereinafter.

DETAILED DESCRIPTION OF EMBODIMENTS

Figure 1A:
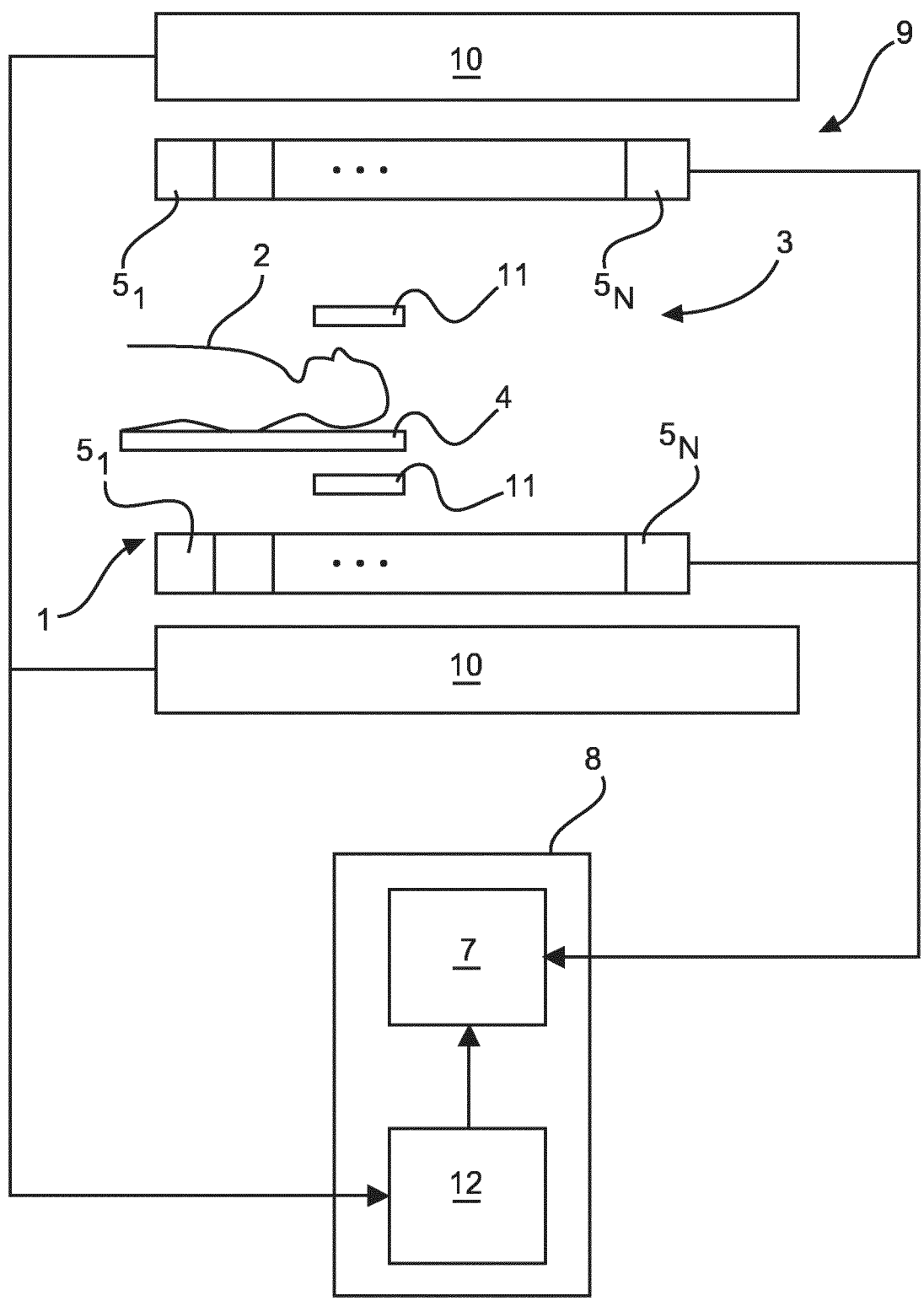
FIG. 1a shows schematically and exemplarily components of a an imaging system comprising a PET scanner and an MRI scanner.

FIG. 1a schematically and exemplarily shows components of an imaging system for imaging an object 2. In particular, the imaging system may be used in a clinical application. In this case, the object 2 to be imaged may be a human or animal body or a part thereof. The imaging system allows for generating images of the object 2 on the basis of PET measurements using a second imaging modality. In the embodiment depicted in FIG. 1a, the second imaging modality is MRI.

Thus, the system includes a PET scanner 1 which may include a substantially cylindrical PET scanner volume 3 accommodating the object 2 during operation of the PET scanner 1. In case the object 2 is a human or animal body, it may be supported by a patient table 4 that is movable into and out of the imaging space 3 by means of a controllable drive unit (not shown in the figures).

Figure 1B:
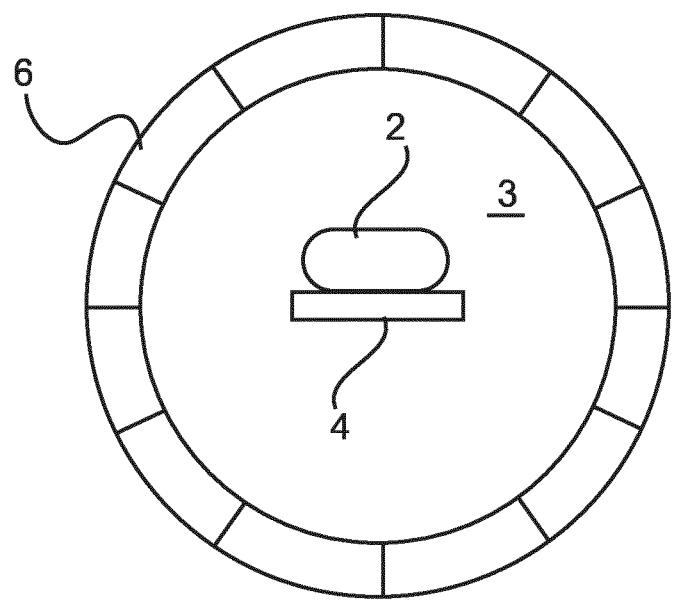
FIG. 1b shows schematically and exemplarily a detector ring of a PET scanner of the imaging system illustrated in FIG. 1a, FIG. 2 shows schematically and exemplarily one embodiment of a PET evaluation unit for evaluating PET measurement data in the system illustrated in FIG. 1a, FIG. 3 shows schematically and exemplarily one embodiment of an attenuation map reconstruction unit included in the PET evaluation unit illustrated in FIG. 2.

The PET scanner volume 3 corresponds to the inner volume defined by a substantially cylindrical detector assembly (which is shown in FIG. 1a in a longitudinal section). The detector assembly may be made up of multiple detector rings $5_1, \ldots, 5_N$ that are arranged adjacent to each other along the central longitudinal axis of the cylindrical PET scanner volume 3. As illustrated in FIG. 1b showing a schematic cross section through one of the detector rings $5_1$, . . . ,$5_N$, each detector ring $5_i$ includes multiple detector elements 6. Each detector element 6 covers a certain angle range of the corresponding detector ring $5_i$ and allows for detecting photons entering the detector element 6 from the PET scanner volume 3 and for measuring their energy. This energy is preferably measured in accordance with so called bins including certain regular energy intervals, where for each detected photon the corresponding energy bin or interval is determined. In FIG. 1b, one of the detector elements is provided with the reference numeral 6. However, individual detector elements are also referred to using their index d hereinafter, where one individual index d is assigned to each detector element.

The detector assembly is coupled to a PET evaluation unit 7 of an evaluation system 8, which processes the measurement data provided by the detector assembly in a way to be further described below in order to produce an attenuation map and an activity map for the object 2 to be monitored. The evaluation system 8 is preferably configured as a data processing system comprising one or more data processing devices, such as computers. In such an evaluation system 8, the PET evaluation unit 7 and its components further described below may be implemented as a computer program that is executed in one or more processors of the evaluation system 8. The program code of the computer program may be stored in a memory of the evaluation system 8 and may be installed on the evaluation system 8 in any suitable way. For instance, it may be preinstalled in the evaluation system 8 and/or it may be installed thereon from a suitable data carrier. Likewise, it may be possible to download the program code to the evaluation system via a data network for installation.

Further, the system shown in FIG. 1a comprises a MRI scanner 9. The MRI scanner includes a MRI unit 10 which is used for exciting nuclear spins in the PET scanner volume 3 and particularly within the object 2 by means of suitable magnetic fields and for receiving signals generated by the excitations. Preferably, the MRI unit 10 surrounds the PET detector assembly in the outer area thereof, i.e. is not included in the PET scanner volume 3 within the detectors rings $5_i$, in order to avoid disturbances of the PET measurements. However, one or more local coils 11 may optionally be arranged in direct vicinity to the object 2 in the inner of the detector assembly 5. One example of such a local coil 11 is a head coil schematically shown in FIG. 1a. The MRI unit 10 and the optional local coils 11 can be configured in a way known to person skilled in the art as such. Therefore, their configuration is not further described here.

The MRI unit 10 and—if present—the local coils 11 are coupled to an MRI evaluation unit 12. In the MRI evaluation unit, the MRI measurements are evaluated to generate one or more three-dimensional MRI images of the object 2. The evaluation can be made in a manner known to the person skilled in the art as such so that a further explanation of the evaluation can be dispensed with. In the embodiment illustrated in FIG. 1a, the MRI evaluation unit 12 is included in the evaluation system 8 together with the PET evaluation unit 7 and my likewise by configured as a computer program executed in the evaluation system 8. However, it is likewise possible to use a MRI evaluation unit 12 which is arranged in a separate device.

The evaluation system 8 further includes and/or is connected to output devices, such as one or more displays, for outputting images of the object 2 generated in the evaluation system 8 and other information to users of the system. Moreover, the evaluation system 8 includes and/or is connected to one or more input means for inputting commands and other information. Such inputs means are particularly utilized by users for controlling the operation of the system.

As said above, the PET measurements are evaluated in the PET evaluation unit 7. In order to capture such measurements, a positron-emitting radiotracer is introduced into the object 2 to be imaged. When a positron is emitted by the radiotracer, the positron and a nearby electron annihilate and produce two annihilation photons, where each annihilation photon has an energy of 511 keV and where the annihilation photons are emitted in opposite directions. These photons produce events in the PET detector assembly which are referred to herein as coincidences. These coincidences can particularly be distinguished in the PET evaluation unit 7 from other events (such as, for example, detection events involving only a single photon), on the basis of the detection times for the two photons. So, the PET evaluation unit 7 may particularly detect a coincidence when two photons are detected substantially simultaneously.

When two annihilation photons travel unimpeded to the PET detector assembly, they cause a so-called true coincidence at two opposing detector elements 6. Such true coincides are used by the PET evaluation unit 7 as one input for calculating the activity and attenuation maps. Such coincidences can particularly be distinguished by the PET evaluation unit 7 from other coincidences on the basis of the energies of the photons, which are substantially 511 keV for each photon.

Further, the evaluation of the PET measurements in the PET evaluation unit 7 is made on the basis of single-scattered coincidences, i.e. coincidences involving one unscattered photon and one photon reaching the PET detector assembly after having undergone Compton scattering a single time. These coincidences can also be distinguished from other coincidences on the basis of the photon energies. So, a photon can lose a maximum of ⅔ of its energy in one scattering event. Hence, all photons having more than ⅓ of the original energy are candidates for single-scattered photons. In one embodiment, the PET evaluation unit 7 selects coincidences involving one photon having an energy of approximately 511 keV (this is the unscattered photon) and a second photon (this is the scattered photon) having energies between approximately 171 keV (=511/3 keV) and an upper threshold somewhat below 511 keV, where the upper threshold may have a value between 505 keV and 510 keV, for example. These coincidences are regarded as single-scattered coincidences.

The measurement data for the true and scattered coincidences are provided in the system in the form of so called sinograms. For the true coincidences one sinogram includes the number of events detected for one so-called Line of Response (LOR), where a LOR involves the two opposing detector elements measuring the true coincidence. The set of all sinograms form the true coincidence data, which are—in short—also referred to as the true coincidences hereinafter. Similarly, the single-scattered coincidence data are made up of sinograms. Each of these sinograms includes the number of single-scattered coincidence events which are detected by two detector elements $d_1$ and $d_2$ and which are detected with an energy $E_1$ of the scattered photon, where $E_1$ denotes the energy bin or interval determined for the scattered photon as explained above.

Figure 2:
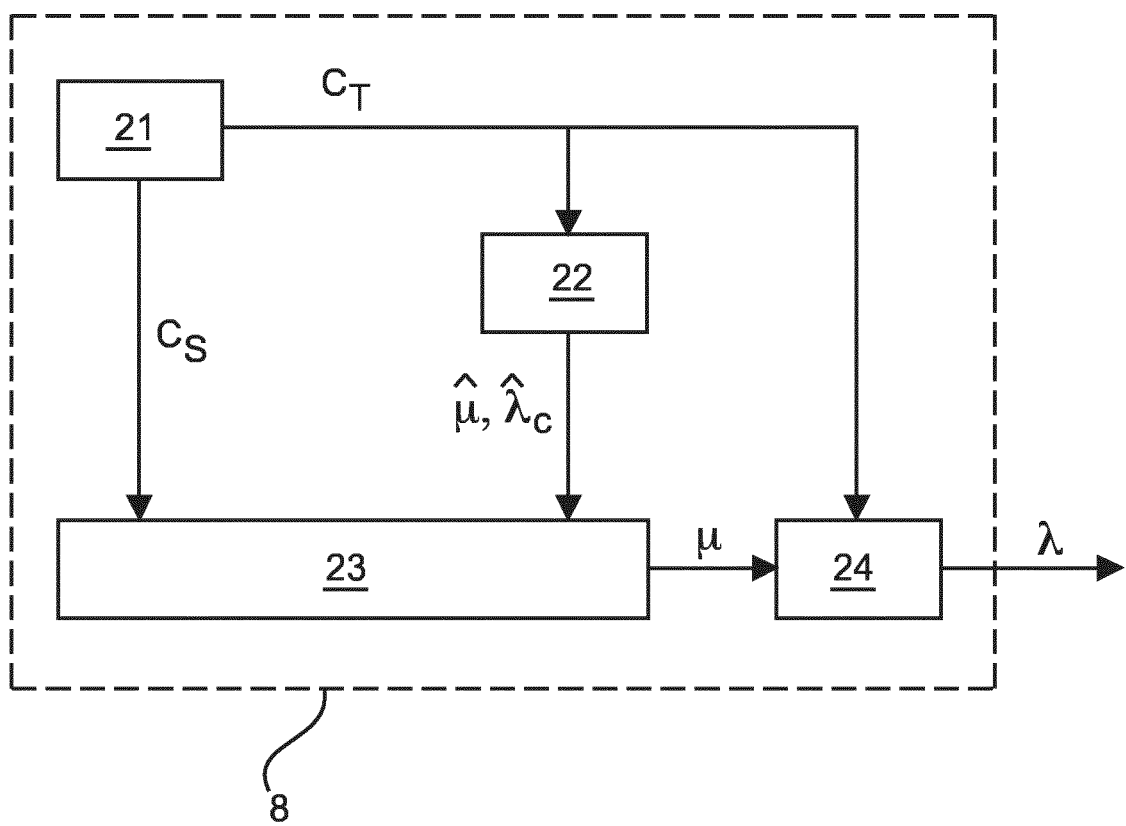

An embodiment of the PET evaluation unit 7 for determining the attenuation map and the activity map for the object 2 on the basis of the measured true and single scattered coincidences is schematically illustrated in FIG. 2. In this embodiment, the PET evaluation unit 7 comprises a block 21, which determines the true coincidences $C_T$ and the single-scattered coincidences $C_S$ in a way described above on the basis of the measurement data provided by the PET detector assembly. The true coincidences $C_T$ are further processed in an estimation unit 22. The estimation unit 22 reconstructs from the true coincidences a first estimate $\hat{\lambda}_C$ of the activity map and a first estimate $\hat{\mu}$ of the attenuation map. For this purpose, the estimation unit 22 may apply the MLAA algorithm as described, for example, in the publication by J. Nuyts et al. already referred to above. As particularly explained in the above-mentioned publication by Y. Berker, F. Kiessling and V. Schulz, such an algorithm allows for determining an estimate $\hat{\lambda}_C$ for the activity distribution which is relatively accurate up to a constant C, i.e. $\hat{\lambda}_C = \hat{\lambda}/C$ (this equation is to be understood such that each activity value in the activity map $\hat{\lambda}$ is divided by the constant C). Moreover, this algorithm allows for determining a rough estimate for $\hat{\mu}$.

The single-scattered coincidences $C_S$ and the estimates $\hat{\lambda}_C$ and $\hat{\mu}$ for the activity map and the attenuation map are provided to an attenuation map reconstruction unit 23, which determines a more accurate attenuation map $\mu$ on the basis of these input data. Using the determined attenuation map $\mu$ and the true coincidences $C_T$, an activity map reconstruction unit 24 then determines the attenuation-corrected activity distribution $\lambda$, which corresponds to the tracer distribution and can be further evaluated for diagnostic purposes, for example. For determining this activity distribution from the true coincidences $C_T$ and the attenuation map $\mu$, any attenuation correction algorithm known to a person skilled in the art may be used.

In the attenuation map reconstruction unit 23, a simulation unit 31 calculates single-scattered coincidences $\hat{C}_S$ in a model calculation on the basis of the first estimate $\hat{\mu}$ for the attenuation map generated in the estimation unit 22, which corresponds to preliminary attenuation map to be updated by the attenuation map reconstruction unit 23, and on the basis of a preliminary activity map $\hat{\lambda}$ and minimizes the difference between the calculated single-scattered coincidences $\hat{C}_S$ and the measured single-scattered coincidences $C_S$. The preliminary activity map $\hat{\lambda}$ may be calculated on the basis of the activity map $\hat{\lambda}_C$ determined in the estimation unit 22 and a preliminary value for the constant C. i.e. $\hat{\lambda} = C \cdot \hat{\lambda}_C$. In the process of minimizing the difference between the calculated and measured single-scattered coincidences, the attenuation map reconstruction unit 23 particularly determines an improved estimate for the attenuation map, which is then provided to the activity map reconstruction unit 24.

Figure 3:
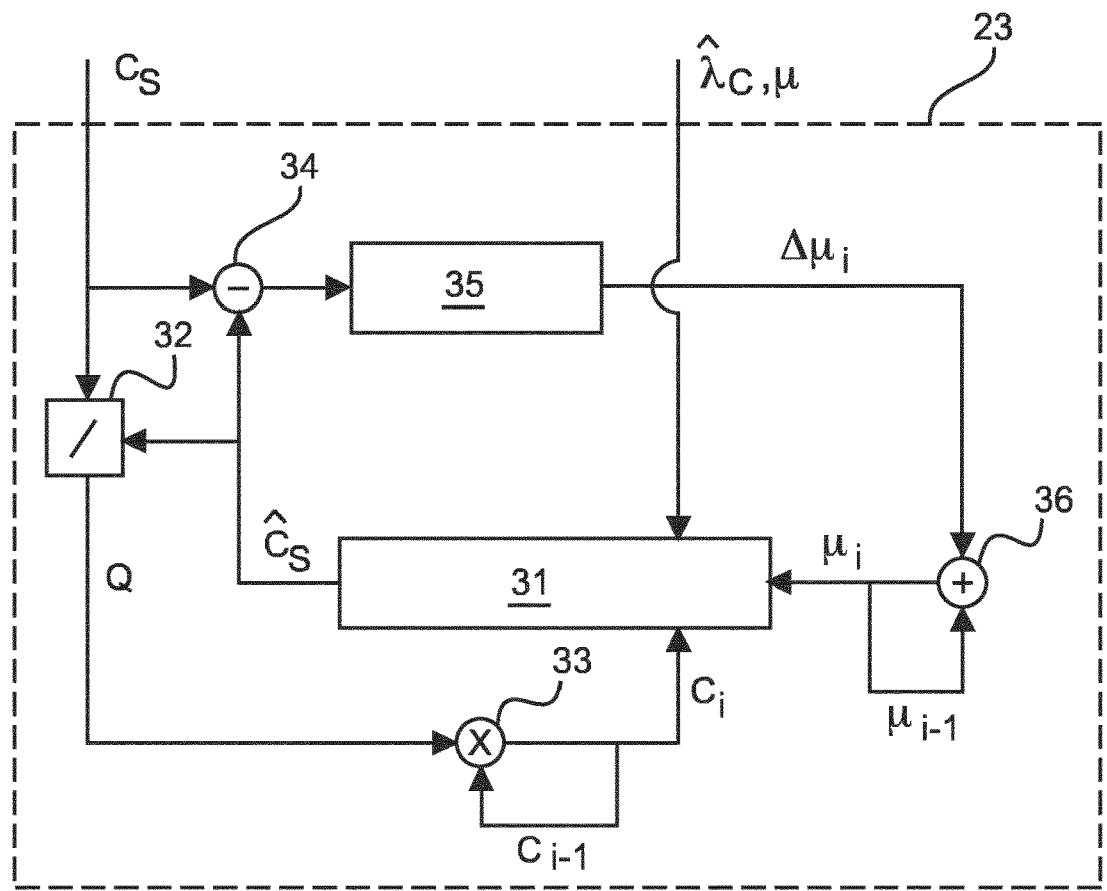

One specific embodiment of the attenuation map reconstruction unit 23 is schematically illustrated in FIG. 3. In this embodiment, the attenuation map reconstruction unit 23 determines the attenuation map $\mu$ using an iterative procedure analogue to the procedure described in the above-mentioned publication by Y. Berker, F. Kiessling and V. Schulz. In each step of the iteration, an updated estimate for the attenuation map $\mu$ and an updated value of the constant C are determined. In FIG. 3, these updated values for the iteration step i are denoted as $\mu_i$ and $C_i$.

The updated value $C_i$ of the constant C is estimated on the basis of a ratio Q between the measured single-scattered coincidences $C_S$ and the calculated single-scattered coincidences $\hat{C}_S$, which may be calculated by the quotient module 32, and on the basis of the constant $C_{i-1}$ used in the preceding step. For determining the ratio between the measured and single-scattered coincidences, the quotient module 32 may determine mean values of the number of events in all sinograms for the measured and calculated single-scattered coincidences and may compute the quotient of these means values. Then, the updated value $C_i$ of the constant C may be calculated by multiplying the ratio Q with the value $C_{i-1}$ determined in the preceding step in the multiplier module 33. This update procedure for the constant C is motivated by the observation that the ratio between the measured single-scattered coincidences $C_S$ and the single-scattered coincidences $\hat{C}_S$ calculated by the simulation unit 31 on the basis of the true attenuation map but on the basis of a wrong constant C' would correspond to the ratio between the correct constant and the wrong constant C', i.e. Q=C/C' when the correct constant is denoted as C. Thus, the next iteration step would produce the correct constant in this update procedure.

Further, the difference between the measured single-scattered coincidences $C_S$ and the calculated single-scattered coincidences $\hat{C}_S$ is calculated in the subtraction module 34. This difference may include differences between the number of events in all sinograms of the measured single-scattered coincidences $C_S$ and the number of events in the corresponding sinograms of the calculated single-scattered coincidences $\hat{C}_S$. In further embodiments, the difference calculated in the subtraction module 34 may include only differences between the numbers of events in selected sinograms of the measured and calculated single-scattered coincidences.

On the basis of the difference, the attenuation map reconstruction unit 32 determines an update $\Delta\mu_i$ for the estimate of the attenuation map. In the embodiment of the attenuation map reconstruction unit 23 shown in FIG. 3, the update is calculated by performing a back-projection of the difference to possible scattering locations of the scattered photons in a back-projection unit 35. On the basis of this back-projection, the back-projection unit 35 generates a difference attenuation map $\Delta\mu_i$. This difference attenuation map $\Delta\mu_i$ is added to the attenuation map estimate $\mu_{i-1}$ determined in the preceding iteration step in order to generate the updated attenuation map estimate $\mu_i$ at the addition module 36. Here, the back-projection and the determination of the difference attenuation map $\Delta\mu_i$ can be made in the manner described in the above-mentioned publication by Y. Berker, F. Kiessling and V. Schulz. However, the invention is not limited to calculate the update in this manner.

On the basis of the updated attenuation map estimate $\mu_i$ and the updated constant $C_i$, the next iteration step is carried out in an analogue way. The iteration is carried out as long as the difference between the measured single-scattered coincidences $C_S$ and the calculated single-scattered coincidences $\hat{C}_S$ is being reduced. When the process does not further reduce this difference in one iteration step, the iteration is stopped and the attenuation map reconstruction unit 23 outputs the estimate of the attenuation map, which leads to the smallest difference between the calculated and the measured single-scattered coincidences. As explained above, this attenuation map may then be used by the activity map reconstruction unit 24 for reconstructing the activity map.

Before explaining the calculation of the single-scattered coincidences in the simulation unit 31 in more detail further below, principles of the measurement of single-scattered coincidences will be described in the following.

For a single-scattered coincidence, the energy of the unscattered photon is 511 keV and the energy of the scattered photon is reduced as a function of the scattering angle $\theta_S$ due to the so-called Compton effect. In particular, the energy $E_S$ of the scattered photon is given by $E_S=E_0/(2-\cos\theta_S)$, where $E_0$ denotes the energy of the unscattered photons. Thus, when a coincident event is detected including an unscattered photon detected at a detector location $\vec{x}_2$ and a scattered photon with a measured energy $\hat{E}_S$ detected at a detector location $\vec{x}_1$, then the set of possible scattering locations $\vec{x}_S$, where the scattering of the scattered photon could have occurred, forms a surface including all positions, where the straight lines connecting the respective scattering location with the detector locations $\vec{x}_1$ and $\vec{x}_2$ have an intersecting angle of $\hat{\theta}_S=\arccos(2-E_0/\hat{E}_S)$.

Figure 4:
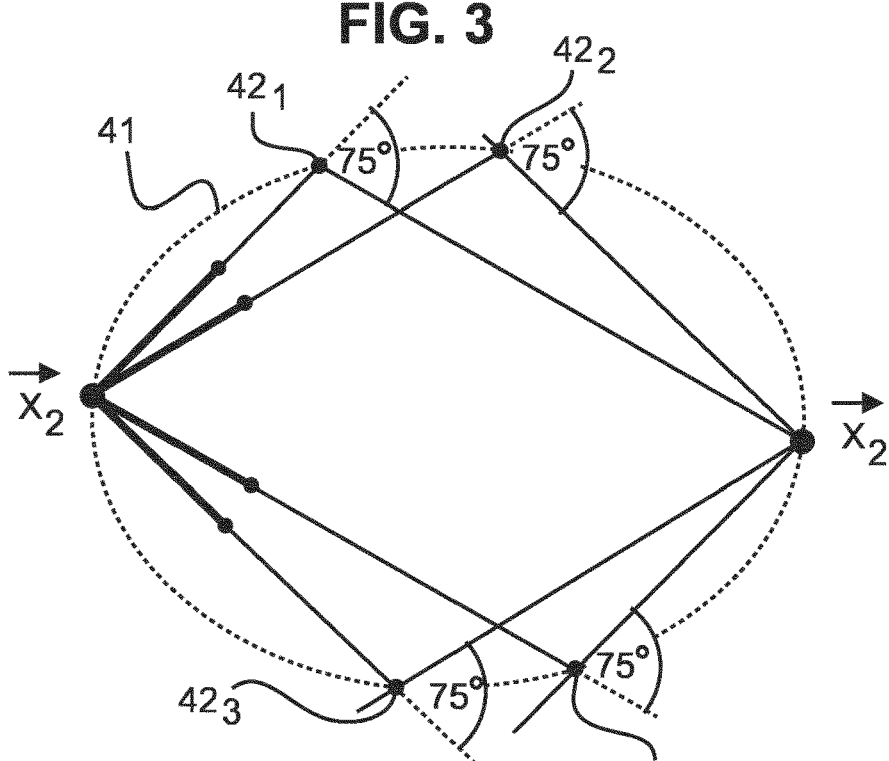
FIG. 4 shows schematically and exemplarily a curve of possible scattering locations for single-scattered coincidences involving a specific energy of the scattered photon, FIGS. 5a and b show schematically and exemplarily a scattering surface for a certain energy of the scattered photon in three dimensions.
Figure 5:
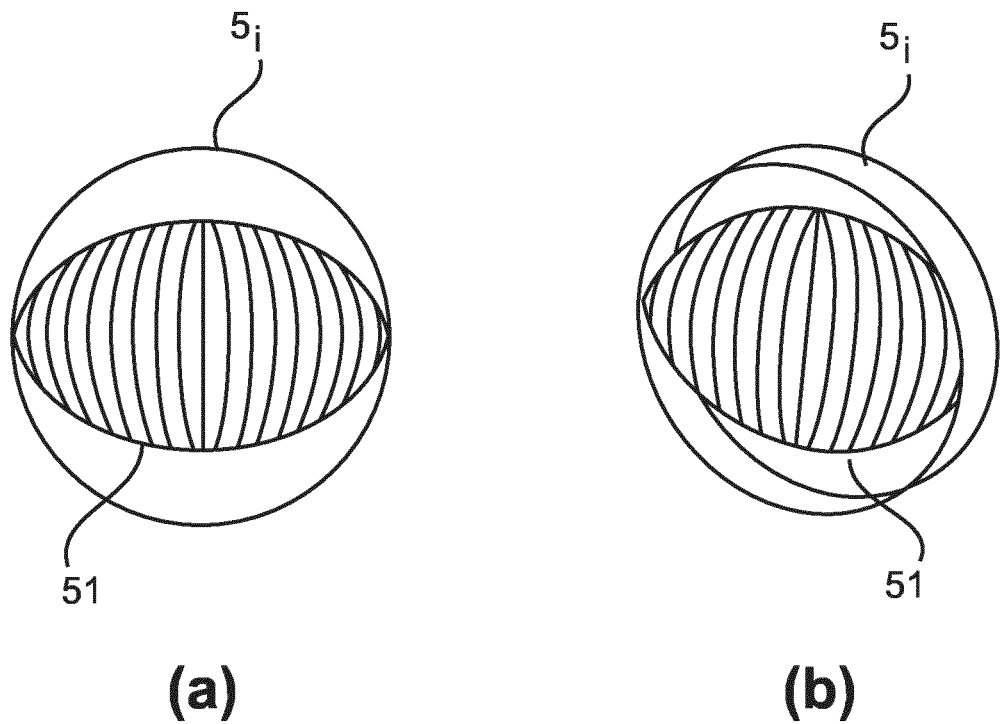

This is further illustrated in FIGS. 4, 5a and 5b. In FIG. 4, a curve 41 of possible scattering locations is schematically illustrated for a cross section through the detector assembly 5 and for a scattering angle $\hat{\theta}_S=75°$ (not shown true to scale in FIG. 4). By way of example, four different scattering locations $42_k$ (k=1, . . . , 4) are shown in FIG. 4, and for each scattering location $42_k$, one possible trajectory of the unscattered photon (thick solid line) and the scattered photon (thin solid line) is shown. For each of these examples, a specific location has been selected for the location of the electron positron annihilation on the connecting line between the respective scattering location $42_k$ and the detector location $\vec{x}_2$ where the unscattered photon is detected. However, it should be understood that the annihilation can occur at any point of this line.

In three dimensions, the possible scattering locations form a surface of revolution. In case of forward scattering (i.e. $\hat{\theta}_S \leq 90°$), this surface is shaped similar to an American football as schematically illustrated in FIGS. 5a and 5b for different views. FIGS. 5a and 5b show one of the detector rings $5_i$ and a three-dimensional surface including possible scattering locations for a certain energy of the scattered photon. For $\hat{\theta}_S=90°$, the possible scattering locations form a sphere, and for backward scattering, the possible scattering locations are more irregularly shaped and their shape can roughly be compared to the shape of an apple.

The number of single-scattered coincidences that can be measured during a time T in a pair of detector modules ($d_1$, $d_2$) at positions $\vec{x}_1$ and $\vec{x}_2$ and with an energy of the scattered photon around $E_1$ and a corresponding scattering angle $\theta_1$ can be estimated as:

$$N^S(d_1, E_1, d_2) \approx T \cdot \Delta E_1 \cdot \left|\frac{d\theta_1}{dE_1}\right| \cdot \quad (1)$$

$$\int_{S(\zeta)} d^2 x_s \left[\int_{L(\vec{x}_2,\vec{x}_S)} \lambda(s_1) ds_1 \cdot \exp\left(-\int_{L(\vec{x}_2,\vec{x}_S)} \mu_{E_0}(s_1) ds_1\right) \times \right.$$

$$\left. \frac{d^2\sigma_{KN}}{d\Omega^2}\bigg|_{\theta_1} \cdot \Omega_1(\vec{x}_S) \cdot \Omega_2(\vec{x}_S) \cdot \right.$$

$$\left. \rho_e(\vec{x}_s) \cdot \exp\left(-\int_{L(\vec{x}_S,\vec{x}_1)} \mu_{E_1}(s_2) ds_2\right) \cdot K_1 \cdot K_2 \right]$$

In this equation, $\Delta E_1$ denotes the width of the energy bin around the energy $E_1$. The surface integral is calculated over the complete surface $S(\zeta)$ of possible scattering locations for the single-scattered coincidences $\zeta=(d_1,d_2,E_1)$. As further discussed in the aforementioned publication by Y. Berker, F. Kiessling and V. Schulz, this integral may be evaluated in an adapted coordinate system, in particular in a kind of bipolar coordinate system, instead of a Cartesian coordinate system.

In the integrand of this integral, the first integral sums the photon emission activity along the line $L(\vec{x}_2,\vec{x}_S)$ between the detection location $\vec{x}_2$ of the unscattered photon and the respective possible scattering location $\vec{x}_S$. Thus, this integral represents the unscattered radiation from the location of the electron positron annihilation to the detector (first photon) and to the scattering location (second photon). The next term in equation (1) represents the attenuation of the unscattered radiation. In this term, $\mu_{E_0}$ represents the linear photon attenuation at the energy $E_0$ (i.e. 511 keV).

In the second line of equation (1), $d\sigma_{KN}/d\Omega$ is the differential Klein-Nishina cross section for Compton scattering. $\Omega_1(\vec{x}_S)$ and $\Omega_2(\vec{x}_S)$ are the solid angles under which the photon scattered at the location $\vec{x}_S$ and the unscattered photon are detected by the respective detector modules $d_1$ and $d_2$. $\rho_e(\vec{x}_s)$ is the electron density at the scattering location $\vec{x}_S$, which influences the probability for Compton scattering at the scattering location $\vec{x}_S$. Thus, the first part of the second line of equation (1) including the aforementioned quantities relates to the percentage of photons emitted on the line $L(\vec{x}_2,\vec{x}_S)$ that are scattered at the location $\vec{x}_S$ in such a way that they can be measured as part of a single-scattered coincidences in the detector modules $d_1$ and $d_2$ and with energy $E_1$.

The next factor in the second line of equation (1), which includes the exponential function, takes account of the attenuation of the scattered radiation traveling along the line $L(\vec{x}_S,\vec{x}_1)$ from the scattering location $\vec{x}_S$ to the detection location $\vec{x}_1$. Here, $\mu_{E_1}$ represents the linear photon attenuation at the energy $E_1$. The factors $K_1$ and $K_2$ at the end of equation (1) represent the detection efficiencies of the detector modules $d_1$ and $d_2$ with respect to the relevant parameters, particularly the energies and the directions of the incoming photons.

On the basis of a model derived from equation (1), the simulation unit 31 may calculate the single-scattered coincidences. This calculation is made on the basis of a discretized coordinate system representing the PET scanner volume 3, i.e. the inner of the PET detector assembly. The discretized coordinate system corresponds to a regular three-dimensional grid which divides the PET scanner volume 3 into volume elements of equal sizes. Conventionally, each volume element would be included in the numerical evaluation as a separate element, which is usually also referred to as voxel. In order to carry out the model calculation of the single-scattered coincidences one attenuation value would, thus, be assigned to each voxel in accordance with the attenuation map. However, this leads to a relatively high number of computation steps to be performed in the simulation unit 31.

In order to reduce the computational complexity, the simulation unit 31 does not assign one attenuation value to each voxel. Rather, the simulation unit 31 merges one or more sets of adjacent voxels in a way to be described below in more detail, and to these merged sets of voxels only one common attenuation value is assigned. Thus, the calculation is based on voxels to which individual attenuation values are assigned and on merged sets of voxels to which a common attenuation value is assigned. These voxels and merged sets of voxels are commonly also referred to as image elements hereinafter. Thus, the term image element refers to one voxel or to one merged set of voxels, where image elements of the latter type are also denoted merged image elements herein. In particular, the number of image elements is, thus, smaller than the number of voxels.

This does effectively mean that the attenuation map used in the model calculation does not exclusively include voxels as smallest elements to which one attenuation value is assigned, but also includes one or more merged image elements.

In each step of the iterative calculation of the attenuation map described above, one attenuation value is assigned to each image element in accordance with the current estimate of the attenuation map and this value may be corrected in each iteration step on the basis of the comparison between the calculated and measured single-scattered coincidences. As explained above, the starting values for the image elements used in the first iteration step can e.g. be determined from the estimate of the attenuation map provided by the estimation unit 22. This can particularly also be done for the image elements including merged sets of voxels. For one such an image element, a mean value of the attenuation values calculated for the included voxels in the estimation unit 22 may be used as a starting value, for example.

For calculating the single-scattered coincidences, the simulation module 31 calculates an estimated number of scattered coincidences for each pair of detector modules $d_1$ and $d_2$ and for each energy bin or interval $E_1$ determined for the scattered photon. This corresponds to a simulation of the single-scattered coincidences measured by means of the PET scanner 1 for the object 2. The calculated data for all scattered coincidences is then combined to form the calculated single-scattered coincidence data which is compared with the measured single-scattered coincidence data in the subtraction module 33 of the attenuation map reconstruction unit 23.

Hereinafter, the combination of two detector modules $d_1$ and $d_2$ measuring a scattered coincidence and an energy $E_1$ of the scattered photon are commonly referred to as a sinogram bin $\sigma=(d_1, d_2, E_1)$. For each sinogram bin, the simulation module 31 may calculate the number of single-scattered events on the basis of a model which substantially follows from equation (1) given above. In one embodiment of the simulation module 31, the scatter amount in the sinogram bin $\sigma$ is calculated in accordance with the formula $$S_\sigma(\mu, \lambda) = \sum_{a,b} \lambda(a) M_{ab}^\sigma(\mu) \mu(b). \quad (2)$$

In order to derive this formula from equation (1), the electron density $\rho_e(\vec{x})$ and the attenuation factors $\mu(\vec{x})$ can be equated with each other. This is justified by the strong correlation between theses quantities. Moreover, the integrals in equation (1) have to be discretized with respect to the aforementioned three-dimensional grid. In this respect, the index b in formula (2) relates to the image elements to which respective attenuation values $\mu(b)$ are assigned in accordance with the (current) estimate $\mu_i$ for the attenuation map in the iterative procedure. The index a preferably relates to the voxels, where one activity value $\lambda(a)$ may be assigned to each voxel in accordance with the current activity map estimate $\lambda_i = C_i \cdot \hat{\lambda}_C$. The sums over a and b in equation (2) preferably run over all indices a and b, i.e. over all voxels and image elements. Thus, by using image elements including sets of merged voxels, the sum over b includes less summands, which leads to a reduction of the required calculation steps for evaluating the sum. When the factors $M_{ab}^\sigma(\mu)$ in equation (2) are together regarded as a matrix $M^\sigma(\mu)$, the number of columns of this matrix is reduced by merging sets of voxels.

Although, the sums over a and b run over all voxels and image elements, not all voxels and image elements contribute to $S_\sigma$. A selection of the relevant voxels and image elements is made by means of the factors $M_{ab}^\sigma(\mu)$. In addition, the factors $M_{ab}^\sigma(\mu)$ weight the voxels and image elements in accordance with their quantitative contribution to $S_\sigma$.

The factors $M_{ab}^\sigma(\mu)$ are composed of a constant geometry factor $G_{ab}^\sigma$ and a variable attenuation factor $A^\sigma(\mu)$ and can be written in the form:

$$M_{ab}^\sigma(\mu) = G_{ab}^\sigma \exp(-A_{ab}^\sigma(\mu)). \quad (3)$$

The factor $G_{ab}^\sigma$ is non-zero only when the image element b covers one or more potential scattering locations, i.e. one or more points on the relevant scattering surface described above. Moreover, $G_{ab}^\sigma$ is non-zero only when the voxel a covers one of the connecting lines between the potential scattering locations within the image element b and the detector element $d_2$ detecting the unscattered photon. The values of the non-zero geometry factors $G_{ab}^\sigma$ particularly reflect the cross section for Compton scattering of a photon originating from the voxel a in the image element b in such a way that the scattered photon is measured with energy $E_1$ in the detector element $d_1$. This cross section particularly results from the Klein-Nishina relation. Moreover, the non-zero geometry factors $G_{ab}^\sigma$ may take account of the detector efficiencies, which are also included in equation (1).

The attenuation factor $A_{ab}^\sigma(\mu)$ can be calculated from attenuation lengths $W_i$ indicating the weight of the image element i with respect to the attenuation of the unscattered photons travelling from the voxel b to the detector module $d_2$ (where the unscattered photon is measured) and to the potential scattering location in the image element a (this is the location where the straight line through the image element b and the detector module $d_2$ intersects the relevant scattering surface) and with respect to the attenuation of the scattered photon travelling from this scattering location to the detector element $d_1$. Using such attenuation lengths, the attenuation factor can be expressed as $$A_{ab}^\sigma(\mu) = \sum_i W_i \cdot \mu(i) \quad (4)$$

This sum corresponds to the line integrals in both exponential functions in equation (1). It may be calculated over all image elements i. In this case, an attenuation length $W_i$ is non-zero only if the image element i covers the connecting lines between the aforementioned potential scattering location in the image element b for a photon originating from voxel a. The non-zero attenuation lengths $W_i$ particularly reflect the distance that the scattered or unscattered photon travels within the relevant image elements. Moreover, the attenuation lengths $W_i$ may take account of the different energies of the unscattered and scattered photons.

For calculating the number of single-scattered coincidences for one sinogram bin $\sigma$, the simulation unit 31 determines each factor $M_{ab}^\sigma(\mu)$ in accordance with its aforementioned decomposition into the geometry factor and the attenuation lengths particularly on the basis of the locations of the corresponding voxel a and the corresponding image element b. Upon having then calculated the number of single-scattered coincidences for each sinogram bin σ, these results are merged to form the calculated single-scattered coincidences $C_S$ which are compared with the measured single-scattered coincidences $C_S$ in the attenuation map reconstruction unit 23.

Figure 6:
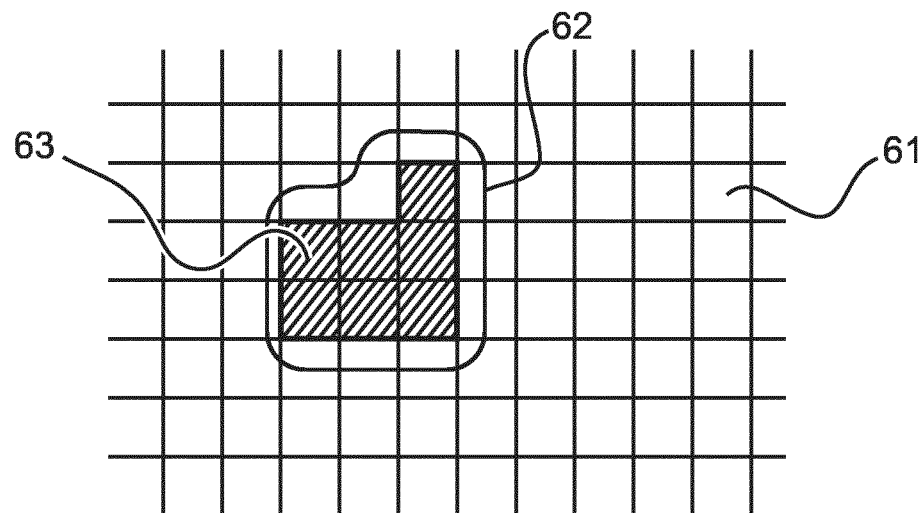
FIG. 6 shows schematically and exemplarily a set of voxels merged to form an image element to which a single attenuation value is assigned in a model calculation of single-scattered coincidences.

In order to merge sets of voxels, to which a common attenuation value is assigned, one embodiment of the simulation unit 31 determines voxels that cover a region of the PET scanner volume 3, which has a substantially homogenous attenuation factor. Such voxels are then merged by the simulation unit 31 to form a single image element to be considered in the calculation of the single-scattered coincidences. By way of example, FIG. 6 further illustrates such a merging for a two-dimensional grid including two-dimensional "voxels" 61. More specifically, FIG. 6 shows a situation in which the simulation unit 31 has identified a region 62 having a substantially homogenous attenuation factor. The voxels included in this region (shown as shaded voxels in FIG. 6) are merged by the simulation unit 31 to form a single image element 63 to be considered in the calculation of the single-scattered coincidences.

For merging sets of voxels in such way, the simulation unit 31 may use one or more of the techniques discussed in the following.

In one embodiment, the simulation unit 31 merges sets of voxels using the attenuation map estimated on the basis of the measured true coincidences in the estimation unit 22. In this embodiment, the simulation unit 31 searches for contiguous regions to which the estimated attenuation map assigns attenuation values which are equal or differ by not more than a predetermined amount. When the simulation unit 31 identifies such a region, it may merge the voxels included in this region to an image element to which a single attenuation value is assigned in the model calculation. Such a merging is made for each region identified in the estimate of the attenuation map.

In a further embodiment, the simulation unit 31 merges sets of voxels using the MRI images generated in the MRI evaluation unit 7 on the basis of the MRI measurements carried out by means of the MRI scanner 9. It is known to a person skilled in the art that such MRI images allow for distinguishing different materials within the object 2. If the object 2 is a human or animal body, it is particularly possible to differentiate between different tissue classes of the tissue within the body. Examples of tissue classes, which can be determined on the basis of the MRI images and on the basis of which voxels can be merged, include cortical bone, fat, soft tissue (i.e. water-dominated tissue) and lung tissue. Further, it is possible on the basis of the MRI images to identify regions including air inside and outside the human body. Voxels included in such regions may likewise be merged.

This possibility is exploited in the present embodiment. Thus, the simulation unit 31 searches for contiguous regions in one or more MRI images of the object 2, which show tissue of the same tissue class or which show air-filled regions. When the simulation unit 31 identifies such a region, it merges the voxels included in this region to an image element to which a single attenuation value is assigned in the model calculation. In further identified regions showing tissue of one common tissue class, the voxels included in these regions are merged in an analogue manner.

In addition or as an alternative to the embodiments described above, the simulation unit 31 may use information about known materials and their positioning in the PET scanner volume 3 to merge sets of voxels to larger image elements. Such known materials include the materials of appliances such as the patient table 4, the local coils 11 positioned within the PET scanner volume 3 (if present) and possible further appliances installed in the PET scanner volume 3. These appliances may be positioned at predetermined locations within the PET scanner volume 3. Thus, it is possible to define the voxels included in contiguous regions covering these appliances and comprising the same material. For each such region, the included voxels may be merged to larger image elements. These image elements may be preconfigured in the simulation unit 31 in accordance with the predetermined positions of the aforementioned appliances in the PET scanner volume 3.

Moreover, there may be material in the PET scanner volume 3 that is outside the object 2 and that is not located at a predetermined position. Examples of such material include pillows supporting an object 2 configured as a human body, local coils 11 which are not positioned at fixed positions and the material of other appliances used in a PET measurements. The position of such materials may be determined in the simulation 31 on the basis of the MRI images. In particular, the MRI images may be produced using so-called Ultra Short Echo-Time (UTE) or Zero Echo-Time (ZTE) sequences. When the simulation unit 31 has determined materials of the aforementioned type in the MRI images it may merge the voxels including the same material to form merged image elements, respectively.

Further, the simulation unit 31 may determine those portions of the PET scanner volume 3, which are not occupied by the object 2 and by the aforementioned appliances. With respect to the aforementioned appliances these portions of the PET scanner volume can again be preconfigured in the simulation unit 31 in accordance with the predetermined positions of these appliances with the PET scanner volume 3. With respect to the object 2, the simulation unit 31 may determine the outline of the object 2 on the basis of the MRI images, if the system includes an MRI scanner 9. On the basis of this outline, it may than determine the portions of the PET scanner volume 3 which are outside the object 2.

The portions of the PET scanner volume 3, which are not covered by the object 2 or an appliance, are filled with the same material, which is usually air. Thus, the simulation 31 may divide these portions of the PET scanner volume 3 into contiguous regions and merge the voxels included in these regions to image elements in the way explained above.

In a further embodiment, the simulation unit 31 only assigns individual attenuation values to voxels within one or more predefined regions of interest within the object 2. Voxels outside these regions of interest may be merged to one or more image elements each including a set of adjacent voxels outside the regions of interest, and to each image element only one attenuation value is assigned in the model calculation. Hereby, the spatial resolution of the attenuation map generated in the attenuation map reproduction unit 23 is effectively reduced in the portions of the attenuation map corresponding to locations outside the region of interest. This means that the differing attenuation values in these portions cannot be distinguished in the generated attenuation map.

The regions of interest may particularly include areas within the object 2 which are of particularly diagnostic interest. So, if the object 2 is a human or animal body, the imaging system may be used to examine a particular organ and/or tissue at a certain location within the body. In this case, the region of interest may include the organ and or the location of interest. The position of this region of interest within the PET scanner volume 3 may be determined by the simulation unit 31 on the basis of the MR images provided by the MRI evaluation unit 12. Upon having determined the position of the region of interest within the PET detector volume 3, the simulation unit 31 identifies the voxels outside the region of interest and merges sets of adjacent voxels outside the region of interest as described above.

In a further variant of the aforementioned embodiment, the attenuation map generated in the PET evaluation unit 7 according to one of the embodiments described above may be combined with an attenuation map generated in different manner and attenuation correction of the activity map may be performed on the basis of the combined attenuation map.

In this respect, some other approaches exist for generating an attenuation map, which are known to yield incorrect estimates for the attenuation map in specific anatomic regions. For instance, in MRI-based approaches, the paranasal sinuses can often not be distinguished from bone tissue, for example. This leads to an incorrect estimate of the attenuation map in the area of the paranasal sinuses. In a further example, a CT scanner may be integrated into the above mentioned system in addition to or as an alternative to the MRI scanner 9, and the CT images generated using the CT scanner may be used to produce the further estimate of the attenuation map. However, it is known that metal streak artifacts in CT images can lead to wrong estimates of the attenuation map. So, a huge fan of rays is usually highlighted in case of metal streak artifacts, and in the areas of such highlighted rays, the attenuation map may not be correctly determined.

When a further estimate for the attenuation map is used in addition to the estimate generated in the attenuation map reproduction unit 23, the regions of interest, in which individual attenuation values are assigned to each voxel by the simulation unit 31, may correspond to those regions in which the further estimate of the attenuation map likely contains errors. Outside these regions, adjacent voxels may be merged by the simulation unit 31 to form one or more combined image elements as described above. Hereby, the attenuation map reconstruction unit 23 determines an attenuation map which has a high spatial resolution only in those regions which are "problematic" in the further estimate of the attenuation map. In order to generate the final attenuation map for carrying out the attenuation correction, the high resolution regions may be taken from the attenuation map generated in the attenuation map reconstruction unit and the other regions may be taken from the further estimate of the attenuation map.

In the embodiments described above, it is possible to determine an estimate for the attenuation map on the basis of single-scattered coincidences with a reduced computational complexity. In this respect, the skilled person will understand that the invention is not limited to the embodiments described above.

In particular, the difference between the calculated single-scattered coincidences and the measured single-scattered coincidences may be minimized in a different way. In principle, any suitable minimization algorithm can be used for minimizing this difference. One example of an alternative algorithm is the function "fminsearch" of the computer program MATLAB, which could be applied to the difference between the calculated and measured single-scattered coincidence data. Using this function, an attenuation map and a constant C minimizing the difference could be calculated. Other suitable algorithms are likewise known to the skilled person.

In addition or as an alternative, the model calculation of the single-scattered coincidences may be made on the basis of another model equation differing from the equation (2) referred to above.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention claimed is:

1. A system for generating an estimate of a photon attenuation map for an object, comprising:
    a Positron Emission Tomography scanner configured to measure single-scattered coincidences originating from the object, the single-scattered coincidences comprising one unscattered photon and one photon scattered one time,
    a simulation module configured to calculate single-scattered coincidences by a numerical model calculation based on a preliminary attenuation map and an estimate of an activity map, the model calculation being made on the basis of a regular grid covering the object, the grid comprising a plurality of grid elements to which attenuation values are assigned in accordance with the preliminary attenuation map, and
    an evaluation unit configured to generate the estimate of the photon attenuation map by adapting at least some attenuation values on the basis of a comparison between the calculated single-scattered coincidences and the measured single-scattered coincidences,
    wherein the simulation module is further configured to determine at least one set of adjacent grid elements on the basis of information obtained independent of the single-scattered coincidences in order to form a merged image element including the set of adjacent grid elements and to assign a single attenuation value to the merged image element in the model calculation.

2. The system as defined in claim 1, wherein the simulation module is further configured to assign an individual attenuation value to at least one grid element not included in the merged image element.

3. The system as defined in claim 1, wherein the Positron Emission Tomography scanner is further configured to measure true coincidences, wherein the evaluation unit is configured to determine a further estimate of a photon attenuation map on the basis of the measurements of the true coincidences and wherein the simulation module is configured to determine the set of adjacent grid elements based on the further estimate of the photon attenuation map.

4. The system as defined in claim 3, wherein the simulation module is configured to determine adjacent grid elements having equal attenuation values in the further estimate of the photon attenuation map and to merge these grid elements to form the merged image element.

5. The system as defined in claim 1, comprising a further scanner for imaging the object in accordance with a further modality different from Positron Emission Tomography, wherein the simulation module is configured to determine the set of adjacent grid elements based on an image of the object generated using the further scanner.

6. The system as defined in claim 5, wherein the further scanner is a Magnetic Resonance Imaging scanner.

7. The system as defined in claim 5, wherein the object is at least a part of a human or animal body and wherein the simulation module is configured to identify within the object a region comprising a tissue of the same tissue class in the image generated using the further scanner and to combine grid elements covering the identified region to form the merged image element.

8. The system as defined in claim 1, wherein the grid further covers a region outside the object, a portion of this region including the same material, and wherein the simulation module is configured to combine grid elements covering the portion of the region to form the merged image element.

9. The system as defined in claim 8, wherein a position of the portion of the region outside the object, which includes the same material, is preconfigured in the simulation unit and/or determined on the basis of the image of the object, which is generated using the further scanner.

10. The system as defined in claim 1, wherein the simulation module is configured to identify grid elements corresponding to a predetermined region of interest within the object and to combine grid elements which do not correspond to the predetermined region of interest, to form the merged image element.

11. The system as defined in claim 1, wherein the evaluation unit is configured to determine the estimate of the photon attenuation map in a series of iteration steps and wherein in each iteration step the evaluation unit determines an updated attenuation map on the basis of a comparison between calculated single-scattered coincidences and the measured single scattered coincidences.

12. The system as defined in claim 11, wherein the evaluation unit is configured to determine in one iteration step a difference between the updated attenuation map and an attenuation map determined in a preceding iteration step, the difference being determined on the basis of a back-projection of a difference between the measured single-scattered coincidences and the calculated single-scattered coincidences.

13. The system as defined in claim 1, wherein the Positron Emission Tomography scanner is further configured to measured true coincidences and wherein the system is configured to determine the estimate of the activity map on the basis of the measured true coincidences.

14. A method for generating an estimate of a photon attenuation map for an object, the method comprising:

operating a Positron Emission Tomography scanner to measure single-scattered coincidences originating from the object, the single-scattered coincidences comprising one unscattered photon and one photon scattered one time, calculating single-scattered coincidences by a numerical model calculation based on a preliminary attenuation map and an estimate of an activity map, the model calculation being made on the basis of a regular grid covering the object, the grid comprising a plurality of grid elements to which attenuation values are assigned in accordance with the preliminary attenuation map, and generating the estimate of the photon attenuation map by adapting at least some attenuation values on the basis of a comparison between the calculated single-scattered coincidences and the measured single-scattered coincidences, wherein at least one set of adjacent grid elements is determined on the basis of information obtained independent of the single-scattered coincidences to form a merged image element including the set of adjacent grid elements and a single attenuation value is assigned to the merged image element in the model calculation.

15. A computer program executable in a processing unit of a system, the computer program comprising program code for causing the processing unit to carry out a method as defined in claim 14.

* * * * *